United States Patent [19]
Muller et al.

[11] Patent Number: 5,690,634
[45] Date of Patent: Nov. 25, 1997

[54] MEDULLARY DRILL HEAD

[75] Inventors: Christof Muller, Berlin, Germany; Peter Christen, Selzach, Switzerland

[73] Assignee: Synthes (U.S.A.), Paoli, Pa.

[21] Appl. No.: 599,505

[22] Filed: Jan. 25, 1996

Related U.S. Application Data

[63] Continuation of Ser. No. 299,965, Sep. 2, 1994, abandoned.

[30] Foreign Application Priority Data

Sep. 15, 1993 [CH] Switzerland ............... 02774/93

[51] Int. Cl.⁶ ..................................... A61B 17/16
[52] U.S. Cl. ..................... 606/80; 606/79; 606/180
[58] Field of Search ........................... 606/79, 80, 81, 606/84, 85, 167, 170, 179, 180

[56] References Cited

U.S. PATENT DOCUMENTS

| | | | |
|---|---|---|---|
| 3,320,957 | 5/1967 | Sokolik | 606/180 |
| 5,100,426 | 3/1992 | Nixon | 606/170 |
| 5,122,134 | 6/1992 | Borzone et al. | 606/80 |
| 5,196,024 | 3/1993 | Barath | 606/170 |
| 5,203,653 | 4/1993 | Kudla | 606/81 |
| 5,366,468 | 11/1994 | Fucci et al. | 606/180 |

*Primary Examiner*—Michael Buiz
*Assistant Examiner*—Daphna Shai
*Attorney, Agent, or Firm*—Fish & Richardson P.C.

[57] ABSTRACT

A drill head for intramedullary drilling has a front part, a middle part and a rear part and is shaped as a hollow body of revolution. The front and rear parts have spiral slots formed with cutting edges. The rear part has an attachment for coupling to a drilling shaft.

17 Claims, 2 Drawing Sheets

_5,690,634_

MEDULLARY DRILL HEAD

This is a continuation of application Ser. No. 08/299,965 filed on Sep. 2, 1994, now abandoned.

FIELD OF THE INVENTION

The invention relates to a drill or reamer head for bone surgery and in particular to a drill or reamer head for use in drilling the medullae of long bones.

BACKGROUND OF THE INVENTION

In osteosynthetic treatment of fractured tubular bones, prior to the implantation of a medullary nail, the medullary space must be drilled or reamed out. To this end first a reamer guide or mandrel is fitted through the medullary segments of the individual bone fragments, over which a hollow, flexible drilling shaft with a solid drilling head is then fitted. A pneumatic drill is normally used to drive the drill shaft. After that a flexible shaft with replaceable heads having exterior diameters of differing sizes is inserted to do the final reaming out of the medullary space. Medullary drill heads can be attached securely onto the flexible shaft, and released from it by means of a simple coupling.

Since according to the state of the art the medullary drill heads (apart from the hollow shaft for the reamer guide which is fully occupied by the guide) are solid, during the drilling procedure a considerable metaphyseal and radial pressure is generated within the medulla of the distal fracture fragment. Peak values for pressure of up to 1500 mm Hg can be produced.

The enormous increase in pressure causes a squeezing of the medullary fat into the transcortical vessels, which is disadvantageous to fracture healing, because the transcortical vessels are impaired in their function not only by the drilling procedure but also by the shifting of the medullary fat. Also, a pressure-induced infiltration of fat into the draining vein system may lead to fat embolisms.

In addition, the temperature rise that accompanies the drilling procedure (with peak values up to 50° C.) is undesirable.

Finally, the drill head frequently becomes jammed in the medullary space; it must then be extracted with special instruments.

SUMMARY OF THE INVENTION

In accordance with the invention, there is provided a hollow drill head which permits dispersal of hydraulic pressure in the distal fracture fragment during drilling of the medulla, thus avoiding the difficulties experienced with prior drilling devices.

In accordance with the invention, a drill or reamer head is provided comprising a hollow body having a front part, a rear part and a middle part, the body having the configuration of a hollow body of revolution, said front and rear parts each having at least one opening and the rear part having means for releasable connection to a flexible drill shaft. Preferably, the front and rear parts have the shape of truncated cones. Preferably the openings are spiral slots having cutting edges.

By using a drill head according to the invention, the pressure that is engendered in front of the drill head during the drilling procedure can be dispersed backward through the openings provided for this purpose in the hollow drill head.

DESCRIPTION OF A PREFERRED EMBODIMENT

Figure 1:
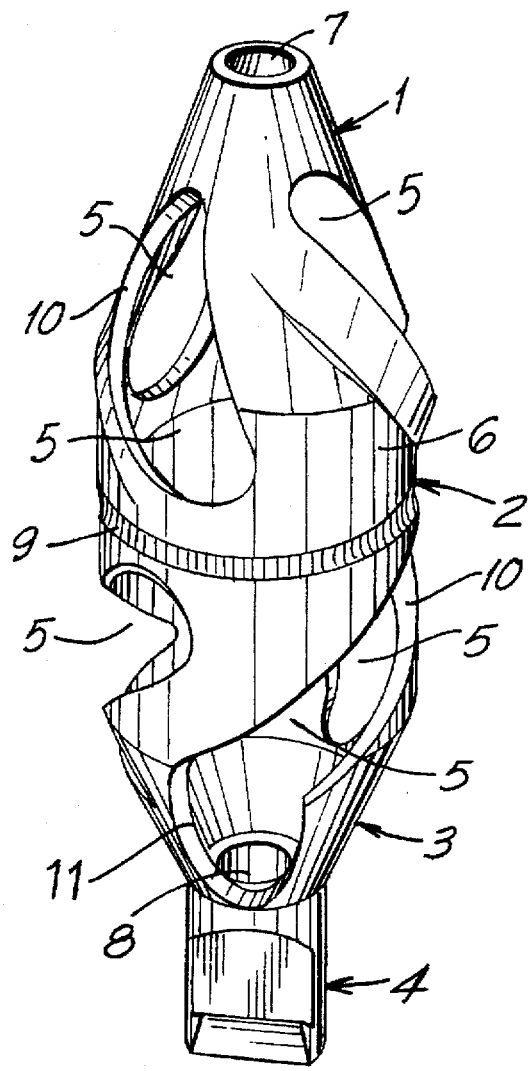
FIG. 1 is a perspective view of a medullary drill or reamer head according to the invention.

Referring to FIG. 1 of the drawings, a medullary drill head essentially consists of a hollow body of revolution with a truncated conically shaped front part 1, a middle part 2, a truncated conically shaped rear part 3 and a coupling piece 4 attached to the rear part, for releasable attachment to a flexible, drivable drill shaft (not shown). The wall thickness of the hollow body of revolution is most advantageously about 1 mm.

The front part 1, rear part 3 and coupling part 4 are equipped with openings such as 7 and 8, through which a drill or reamer guide or mandrel (not shown) with the same diameter can be inserted.

Figure 2:
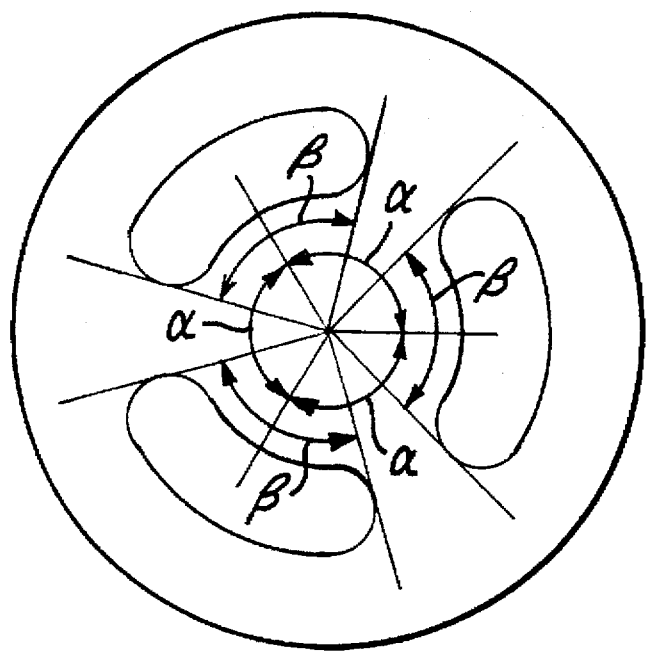
FIG. 2 is a schematic top plan view of the reamer head of FIG. 1 indicating the angular positioning and size of the openings which are shown symbolically.

In front part 1 as well as the section of middle part 2 which adjoins part 1, in the shell 6 of the hollow body of revolution, three openings 5 in the form of spirally shaped slots, are placed 120° apart; that is, as shown in FIG. 2, the angular distance α, from the same point on one slot, for example the upper tip or the center, to the same point on adjacent slots, is 120°. In rear part 3, as well as in the adjoining section of middle part 2, approximately symmetrical with the slots in the front part, three openings 5' in the form of spiral slots, are arranged 120° apart. As shown in FIG. 2, the slots 5, 5' extend over a sector β of about 60°–100°, preferably about 80°–100°, and most preferably about 90°. At their lower ends the slots in the rear part are preferably enlarged as at 11 to prevent clogging of the drill head.

Figure 4:
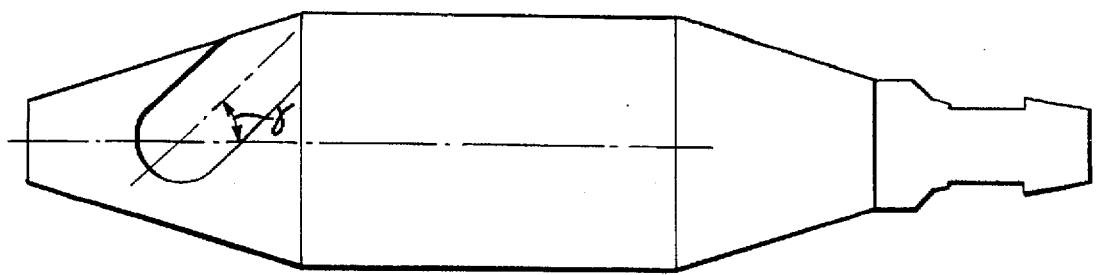
FIG. 4 is a schematic simplified side elevational view of the drill head of FIGS. 1 and 2 indicating the inclination of an opening to the axis of the head.

As indicated in FIG. 4, the pitch angle γ, i.e. the angle of inclination of the helically shaped slots to the longitudinal axis of the head is from about 20° to about 40°, preferably about 25° to about 35°, most preferably about 30°.

Figure 3:
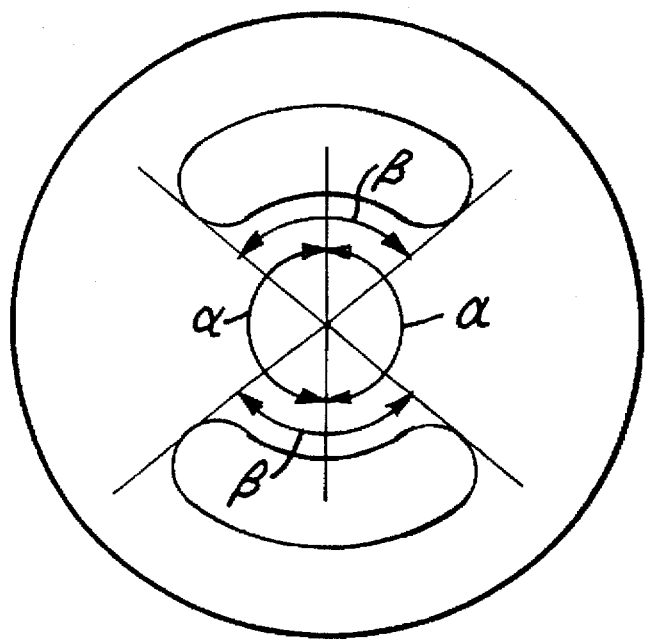
FIG. 3 is a schematic top plan view of a variant of the drill head of FIG. 2.

Instead of the three slots displaced by 120°, as shown in FIG. 3, two slots displaced by 180° may be used.

The slots 5, 5' are configured so as to have cutting edges 10, similar to a grater. Preferably the edges 10 which are oriented toward coupling piece 4 are raised up, for example, by bending them back.

Coupling piece 4 is shaped according to the state of the art, and can be equipped with any suitable coupling system for the drill shaft to be affixed to it.

The two halves of the hollow body of revolution can be made separately and then joined to each other along weld seam 9. The walls of the body may be about 0.5 to about 2 mm thick, preferably about 0.8 to about 1.2 mm. At least 50%, and preferably at least 70%, of the head is hollow.

What is claimed is:

1. A drill head for drilling out the medulla of a tubular bone comprising a hollow body of revolution having a front part, a middle part and a rear part, each of the front and rear parts having spiral slots with cutting edges, the middle part providing an area free from slots separating the slots of the front and rear parts from one another and the rear part having coupling means for attachment to a drill.

2. The drill head claimed in claim 1 wherein the front part has the shape of a truncated cone.

3. The drill head claimed in claim 2 wherein the rear part has the shape of a truncated cone.

4. The drill head claimed in claim 3 wherein each spiral slot occupies a sector of the body of revolution of about 60° to about 100°.

5. The drill head claimed in claim 4 wherein the sector is about 80° to about 100°.

6. The drill head claimed in claim 1 wherein the cutting edges face toward the coupling means.

7. The drill head claimed in claim 6 wherein the drill head has a central axis and the spiral slots are inclined to the axis of the drill head at an angle of about 20° to about 40°.

8. The drill head claimed in claim 7 wherein the spiral slots are inclined to the axis of the drill head at an angle of about 25° to 35°.

9. The drill head claimed in claim 1 wherein the front part comprises two spiral slots extending into the middle part, about 180° apart.

10. The drill head claimed in claim 9 wherein the rear part comprises two spiral slots extending into the middle part, about 180° apart.

11. The drill head claimed in claim 1 wherein the front part has three slots about 120° apart extending into the middle part.

12. The drill head claimed in claim 11 wherein the rear part has three slots, about 120° apart extending into the middle part.

13. The drill head claimed in claim 1 wherein the body of revolution comprises a shell from about 0.5 to about 2 mm thick.

14. The drill head claimed in claim 13 wherein the shell is from about 0.8 to about 1.2 mm thick.

15. The drill head claimed in claim 1 and comprising openings in the front part and in the rear part for receiving a guide wire.

16. The drill head claimed in claim 1 wherein at least 50% of the total volume of the body of revolution is hollow.

17. The drill head claimed in claim 16 wherein at least 70% of the total volume of the body of revolution is hollow.

\* \* \* \* \*